United States Patent [19]
Brimhall

[11] Patent Number: 5,879,334
[45] Date of Patent: Mar. 9, 1999

[54] CONTROL FORWARD INTRODUCER NEEDLE AND CATHETER ASSEMBLY

[75] Inventor: Greg L. Brimhall, West Jordan, Utah

[73] Assignee: Becton Dickinson and Company, Franklin Lakes, N.J.

[21] Appl. No.: 643,439

[22] Filed: May 8, 1996

Related U.S. Application Data

[63] Continuation of Ser. No. 405,464, Mar. 16, 1995, abandoned.

[51] Int. Cl.[6] .................................................... A61M 5/18
[52] U.S. Cl. ............................................ 604/165; 604/164
[58] Field of Search .................................... 604/116, 117, 604/164, 165, 281, 282, 177

[56] References Cited

U.S. PATENT DOCUMENTS

| | | | |
|---|---|---|---|
| 3,046,984 | 7/1962 | Eby | 128/214 |
| 3,547,119 | 12/1970 | Hall et al. | 128/214.4 |
| 3,589,361 | 6/1971 | Loper et al. | 128/214.4 |
| 4,099,528 | 7/1978 | Sorenson et al. | 128/214.4 |
| 4,149,539 | 4/1979 | Cianci | 128/325 |
| 4,324,236 | 4/1982 | Gordon et al. | 128/214.4 |
| 4,326,519 | 4/1982 | D'Alo et al. | 128/214.4 |
| 4,353,369 | 10/1982 | Muetterties et al. | 128/214.4 |
| 4,362,156 | 12/1982 | Feller et al. | 604/165 |
| 4,419,094 | 12/1983 | Patel | 604/93 |
| 4,496,348 | 1/1985 | Genese et al. | 604/167 |
| 4,531,935 | 7/1985 | Berryessa | 604/45 |
| 4,813,939 | 3/1989 | Marcus | 604/177 |
| 4,834,708 | 5/1989 | Pillari | 604/165 |
| 5,176,662 | 1/1993 | Bartholomew et al. | 604/283 |
| 5,267,971 | 12/1993 | Brimhall | 604/177 |
| 5,269,764 | 12/1993 | Vetter et al. | 604/167 |
| 5,306,243 | 4/1994 | Bonaldo | 604/86 |
| 5,312,359 | 5/1994 | Wallace | 604/164 |
| 5,391,152 | 2/1995 | Patterson | 604/165 |

FOREIGN PATENT DOCUMENTS

| | | |
|---|---|---|
| 2088215 | 11/1984 | United Kingdom. |
| WO 92/08502 | 5/1992 | WIPO. |
| WO 95/06488 | 3/1995 | WIPO. |

*Primary Examiner*—Sam Rimell
*Attorney, Agent, or Firm*—Eric M. Lee

[57] ABSTRACT

The catheter includes a catheter hub at its proximal end having a pair of spaced apart squeeze grips radially extending from the catheter hub. The needle is connected at its proximal end to a needle hub. The needle hub has a circumferentially extending bump formed adjacent to its distal end. The needle and needle hub fit within a slide assembly comprising a tubular portion with a circumferentially extending groove formed therein and a radially extending fin extending from the outer surface of the tubular portion of the slide assembly. The bump of the needle hub mates in the groove of the slide assembly to allow rotation of the needle hub with respect to the slide assembly. However, the bump and the groove are dimensioned to prevent relative axial movement between the needle hub and the slide assembly. The fin on the slide assembly extends forward so as to be positioned between and extend beyond the pair of squeeze grips on the catheter hub. This arrangement allows the distal tip of the needle to be retracted into the catheter with a simple motion by the healthcare worker.

7 Claims, 4 Drawing Sheets

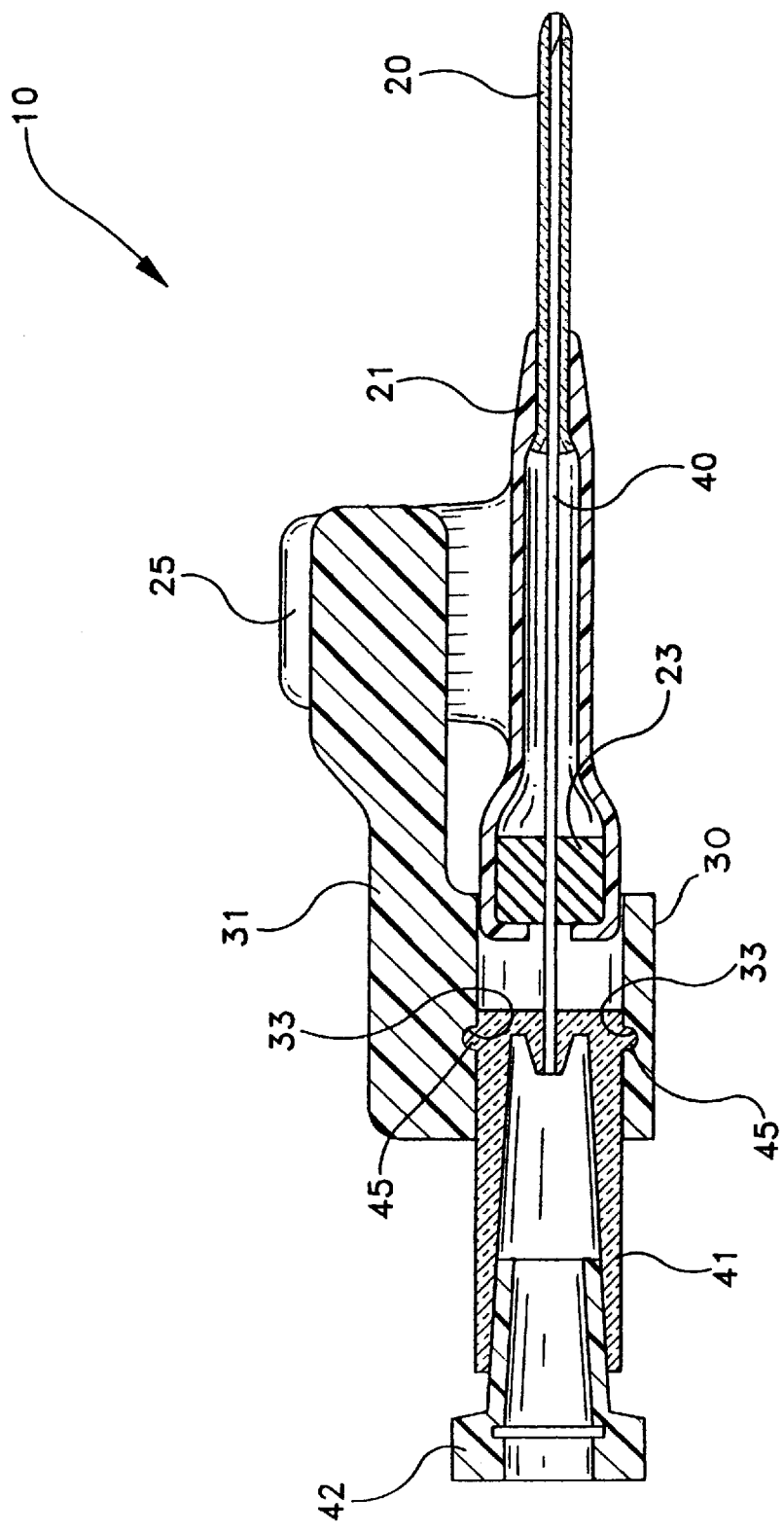

CONTROL FORWARD INTRODUCER NEEDLE AND CATHETER ASSEMBLY

This is a continuation of application Ser. No. 08/405,464, filed Mar. 6, 1995 abandoned.

BACKGROUND OF THE INVENTION

This invention relates to a catheter and introducer needle assembly. Catheters, particularly intravenous (IV) catheters are used for directing fluid into or withdrawing fluid from a patient. The most common type of IV catheter is an over-the-needle catheter. As its name implies, an over-the-needle IV catheter is mounted over an introducer needle having a sharp distal tip. With the distal tip of the introducer needle extending beyond the distal tip of the catheter, the assembly is inserted through the patient's skin into a vein. Once placement of the assembly in the vein is verified by flashback of blood in the needle, the needle is withdrawn leaving the catheter in place. The proximal end of the catheter typically has a hub that is designed to be connectable to an IV fluid supply line after insertion of the catheter in a patient.

Although typical IV catheter and introducer needle assemblies generally perform their functions satisfactorily, they do have certain drawbacks. For example, the entire procedure of properly placing an IV catheter into a patient can be cumbersome and awkward and require the use of both hands of the healthcare worker. In addition, prior IV catheter and introducer needle assemblies do not provide a simple means of breaking adhesion between the needle and IV catheter prior to insertion of the assembly into the patient. Adhesion can occur because the inner diameter of the catheter is typically less than the outer diameter of the needle to provide a smaller profile for the assembly and facilitate insertion of the IV catheter into a patient. Thus when the assembly is sterilized and is not used for a period of time after sterilization, the catheter can adhere to the introducer needle. In addition, the lubricant that is used on the introducer needle and catheter can contribute to tip adhesion. Breaking adhesion prior to insertion of the assembly into the patient facilitates removal of the introducer needle once the IV catheter has been properly placed. Finally, prior IV catheter and introducer needle assemblies do not allow for the flexibility of allowing an IV fluid supply line to be connected to the IV catheter prior to insertion of the IV catheter and introducer needle assembly into a patient.

SUMMARY OF THE INVENTION

It is therefore an object of this invention to provide an IV catheter and introducer needle assembly that is easy to control and insert into a patient.

It is another object of this invention to provide an IV catheter and introducer needle assembly that allows adhesion between the IV catheter and the needle to be broken prior to insertion of the assembly into a patient.

It is yet a further object of this invention to provide an IV catheter and introducer needle assembly that allows an IV fluid supply line to be connected to the catheter prior to insertion of the assembly into a patient.

The above and other objects are satisfied by the IV catheter and introducer needle assembly of this invention. The catheter includes a catheter hub at its proximal end having a pair of spaced apart squeeze grips radially extending from the catheter hub and generally aligned with the longitudinal axis of the catheter. The needle is connected at its proximal end to a needle hub. The needle hub has a circumferentially extending bump formed adjacent to its distal end. The needle and needle hub fit within a slide assembly comprising a tubular portion with a circumferentially extending groove formed therein and a radially extending fin extending from the outer surface of the tubular portion. The radially extending fin is generally aligned with the longitudinal axis of the needle. The bump of the needle hub mates in the groove of the slide assembly to allow rotation of the needle hub with respect to the slide assembly. However, the bump of the needle hub and the groove of the slide assembly are dimensioned to prevent relative axial movement when the bump is mated in the groove. The fin on the slide assembly extends forward so as to be positioned between and extend beyond the pair of spaced apart squeeze grips on the catheter hub. This arrangement allows the distal tip of the needle to be retracted into the catheter with a simple motion by the healthcare worker.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numbers refer to like elements and in which:

FIG. 5 is a cross-sectional view of the invention similar to the view in FIG. 2 after the distal tip of the needle has been retracted into the catheter.

DETAILED DESCRIPTION OF THE INVENTION

Figure 1:
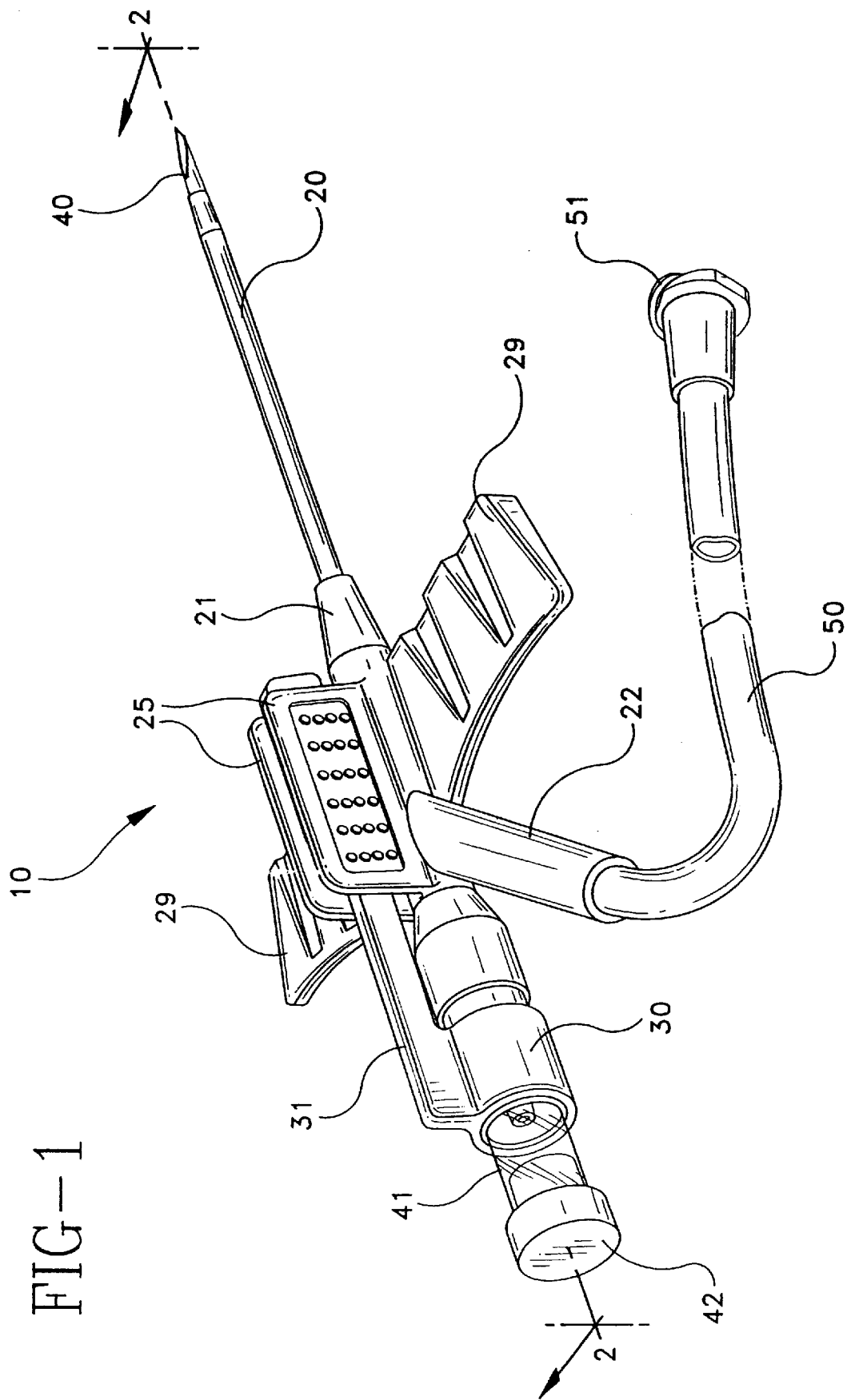
FIG. 1 is a perspective view of the IV catheter and introducer needle assembly of this invention.

The IV catheter and introducer needle assembly 10 of this invention is shown in FIG. 1. This assembly includes catheter 20 affixed to catheter hub 21, slide assembly 30 and needle 40 affixed to needle hub 41. Needle hub 41 can take the form of a flashback chamber having a vent plug 42 affixed thereto.

Catheter hub 21 includes a side port 22 which has an extension tube 50 connected thereto. The proximal end of extension tube 50 includes a standard luer lock adaptor 51 to allow the connection of an IV fluid supply line to extension tube 50. Side port 22 is in fluid communication with the lumen of catheter 20 so that fluid infused through extension tube 50 will pass into the patient once catheter 20 is properly positioned in the patient. The proximal end of catheter hub 21 is sealed with an elastomeric plug 23, such as silicone, (see FIGS. 2 and 5) to ensure that fluid does not leak out of the proximal end of catheter hub 21.

Catheter hub 21 also includes at least one and preferably a pair of spaced apart squeeze grips 25 that extend radially from catheter hub 21. Squeeze grips 25 are generally aligned with the longitudinal axis of catheter 20. The distance that squeeze grips 25 are spaced apart should be sufficient to allow the radially extending fin 31 of slide assembly 30 to easily pass there between and still allow a healthcare worker to grasp fin 31 by squeezing squeeze grips 25 between a thumb and forefinger. Preferably this distance is about 0.070 inches. Squeeze grips 25 should be large enough to allow the healthcare worker to easily grasp them. Catheter hub 21 can also include a pair of wings 29 if desired. These wings 29 can be taped to the patient's skin to ensure that catheter 20 remains in place once it has been inserted into a patient.

Figure 2:
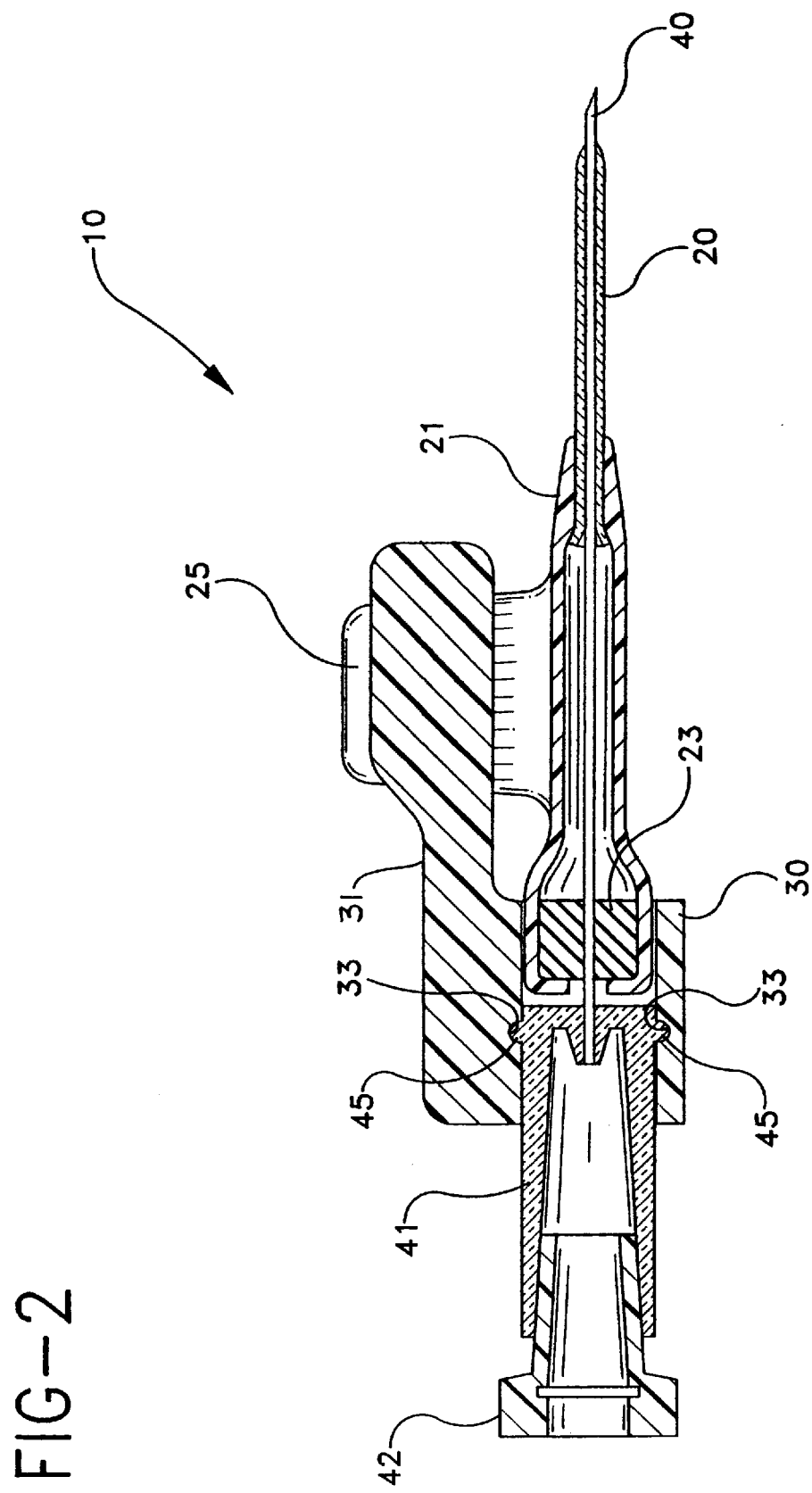
FIG. 2 is a cross-sectional view of the invention taken along line 2—2 in FIG. 1 showing the invention prior to insertion of the invention into a patient.
Figure 3:
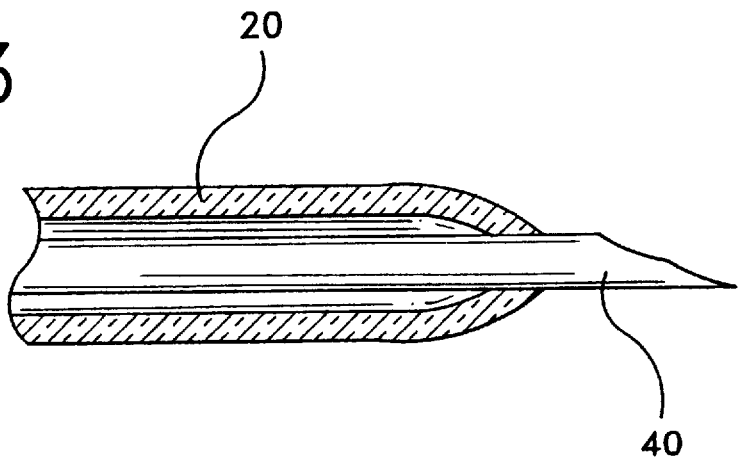
FIG. 3 is an enlarged view of the distal tip of the assembly of this invention shown in FIG. 2.
Figure 4:
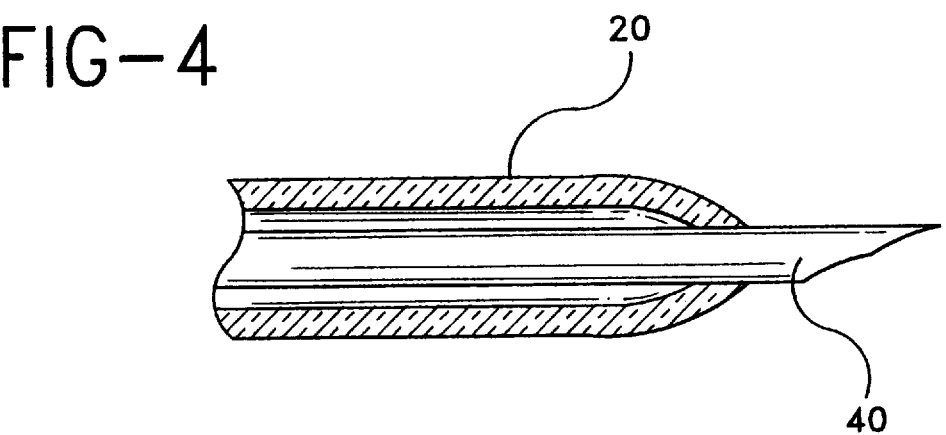
FIG. 4 is an enlarged view of the distal tip of the assembly of this invention shown in FIG. 2 showing the rotation of the needle with respect to the catheter.

Introducer needle 40 has its proximal end connected to needle hub 41 which can take the form of a flashback chamber as shown in FIGS. 1,2 and 5. The proximal end of needle hub 41 includes a vent plug 42 that facilitates the flashback of blood into needle hub 41 when needle 20 is inserted into a patient's vein. The exterior of needle hub 41 defines a circumferentially extending bump 45 whose purpose will be described hereinafter.

Needle hub 41 and needle 40 fit within slide assembly 30. Radially extending fin 31 extends beyond the distal end of slide assembly 30 and is generally aligned with the longitudinal axis of needle 40. Preferably fin 31 extends beyond slide assembly by about ¼ inches. The inner surface of slide assembly 30 includes a circumferentially extending groove 33 that cooperates with bump 45 to maintain the relative axial position between needle hub 41 and slide assembly 30. However, bump 45 and groove 33 are dimensioned to allow needle hub 41 to rotate with respect to slide assembly 30. This in turn allows needle 40 to rotate with respect to catheter 20 when needle 40 has been inserted through elastomeric plug 23 and catheter hub 21 into catheter 20. Such rotation of needle 40 breaks any adhesion between needle 40 and catheter 20.

Figure 6:
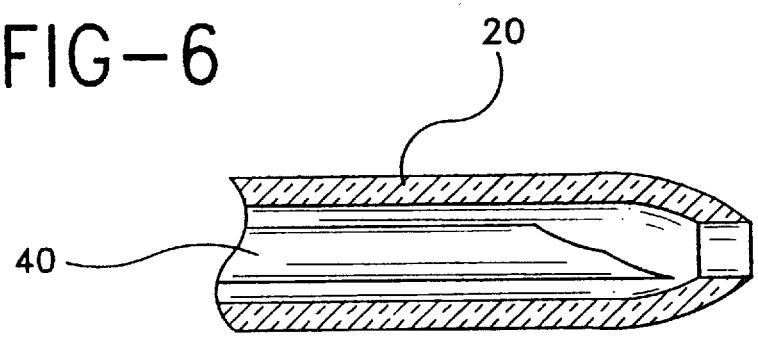
FIG. 6 is an enlarged view of the distal tip of the invention shown in FIG. 5 showing the location of the distal tip of the needle with respect to the distal tip of the catheter.

When needle 40 is inserted completely into catheter 20, the distal tip of needle 40 extends beyond the distal tip of catheter 20 as shown in FIG. 2. In addition, the distal end of fin 31 extends beyond the distal end of squeeze grips 25 as shown in FIG. 2. In this arrangement, catheter and introducer needle assembly 10 is ready for insertion into a patient. The healthcare worker squeezes squeeze grips 25 and thus maintains the relative axial position of needle 40 with respect to catheter 20. Because squeeze grips 25 are close to the distal tip of needle 40, insertion of catheter and introducer needle assembly 10 into a patient is relatively simple and can be accomplished by one hand of the healthcare worker. After catheter and introducer needle assembly 10 has been inserted into a vein, flashback of blood will be observed in needle hub 41. At this point, the healthcare worker can simply push the distal end of fin 31 in the proximal direction to shield the distal tip of needle 40 inside catheter 20 See FIGS. 5 and 6. By shielding the distal tip of needle 40 inside catheter 20, catheter 20 can be advanced into the vein without needle 40 puncturing the vein again. Needle 40 provides column strength to catheter 20 as it is advanced into the vein. Needle 40 can then be removed from catheter hub 21 leaving catheter 20 in place in the patient.

Thus it is seen that an IV catheter and introducer needle assembly is provided that is easy to control and can be inserted into the patient by one hand, that allows adhesion between the IV catheter and the introducer needle to be broken prior to insertion of the assembly into the patient and that allows an IV fluid supply line to be connected to the catheter prior to insertion of the assembly into a patient.

I claim:

1. A catheter and introducer needle assembly, comprising:

a catheter having a proximal end and a distal end;

a catheter hub with a proximal end and a distal end connected to the proximal end of the catheter;

an introducer needle having a proximal end and a distal end disposed inside the catheter;

a needle hub having a proximal end and a distal end connected to the proximal end of the needle, the needle hub defining a circumferentially extending bump; and a slide assembly disposed about the needle hub, the slide assembly defining a circumferentially extending groove that mates with the bump to allow relative rotational movement between the needle hub and the slide assembly but prevents substantial relative axial movement between the slide assembly and the needle hub.

2. The catheter and introducer needle assembly of claim 1 wherein the catheter hub defines aside port located distally of the elastomeric plug and in fluid communication with the catheter.

3. The catheter and introducer needle assembly of claim 1 further comprising an elastomeric plug affixed to and sealing the proximal end of the catheter hub.

4. An introducer needle assembly, comprising:

an introducer needle having a proximal end and a sharp distal end;

a needle hub having a proximal end and a distal end connected to the proximal end of the needle;

a slide assembly operatively connected to the needle hub; and a means associated with the needle hub and the slide assembly for allowing relative rotational movement between the needle hub and the slide assembly and preventing substantial relative axial movement between the slide assembly and the needle hub.

5. A catheter and introducer needle assembly, comprising:

a catheter having a proximal end and a distal end;

a catheter hub with a proximal end and a distal end connected to the proximal end of the catheter, the catheter hub including at least one radially extending squeeze grip;

an introducer needle having a proximal end and a distal end disposed inside the catheter;

a needle hub having a proximal end and a distal end connected to the proximal end of the needle, the needle hub defining a circumferentially extending bump; and a slide assembly disposed about the needle hub, the slide assembly including a radially extending fin and defining a circumferentially extending groove that mates with the bump to allow relative rotational movement between the needle hub and the slide assembly but prevents substantial relative axial movement between the slide assembly and the needle hub.

6. The catheter and introducer needle assembly of claim 5 wherein when the distal end of the needle extends beyond the distal end of the catheter a distal end of the fin extends beyond a distal end of the squeeze grip.

7. The catheter and introducer needle assembly of claim 6 wherein the catheter hub includes a pair of spaced apart radially extending squeeze grips.

\* \* \* \* \*